US007589337B2

(12) United States Patent
Bykanov et al.

(10) Patent No.: US 7,589,337 B2
(45) Date of Patent: *Sep. 15, 2009

(54) LPP EUV PLASMA SOURCE MATERIAL TARGET DELIVERY SYSTEM

(75) Inventors: Alexander N. Bykanov, San Diego, CA (US); J. Martin Algots, San Diego, CA (US); Oleh V. Khodykin, San Diego, CA (US); Oscar Hemberg, Stockholm (SE); Norbert R. Bowering, San Diego, CA (US)

(73) Assignee: Cymer, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/075,631

(22) Filed: Mar. 12, 2008

(65) Prior Publication Data

US 2008/0179549 A1 Jul. 31, 2008

Related U.S. Application Data

(63) Continuation of application No. 11/174,443, filed on Jun. 29, 2005, now Pat. No. 7,372,056.

(51) Int. Cl.
*A61N 5/06* (2006.01)
*G01J 3/10* (2006.01)
*H05G 2/00* (2006.01)

(52) U.S. Cl. .............................. 250/504 R; 250/495.1; 250/503.1; 378/119; 372/5; 372/18; 372/70; 372/38.02; 372/9; 359/334; 359/338

(58) Field of Classification Search ............. 250/495.1, 250/503.1, 504 R; 378/119; 372/5, 18, 70, 372/38.02, 9; 359/334, 338
See application file for complete search history.

(56) References Cited

U.S. PATENT DOCUMENTS 2,759,106 A 8/1956 Wolter ......................... 250/53

(Continued)

FOREIGN PATENT DOCUMENTS

JP 02-105478 4/1990

(Continued)

OTHER PUBLICATIONS

Andreev, et al., "Enhancement of laser/EUV conversion by shaped laser pulse interacting with Li-contained targets for EUV lithography", *Proc. of SPIE*, 5196:128-136, (2004).

(Continued)

*Primary Examiner*—Jack I Berman
*Assistant Examiner*—Meenakshi S Sahu

(57) ABSTRACT

An EUV light generation system and method is disclosed that may comprise a droplet generator producing plasma source material target droplets traveling toward the vicinity of a plasma source material target irradiation site; a drive laser; a drive laser focusing optical element having a first range of operating center wavelengths; a droplet detection radiation source having a second range of operating center wavelengths; a drive laser steering element comprising a material that is highly reflective within at least some part of the first range of wavelengths and highly transmissive within at least some part of the second range of center wavelengths; a droplet detection radiation aiming mechanism directing the droplet detection radiation through the drive laser steering element and the lens to focus at a selected droplet detection position intermediate the droplet generator and the irradiation site.

11 Claims, 3 Drawing Sheets

U.S. PATENT DOCUMENTS

| | | | | |
|---|---|---|---|---|
| 3,150,483 | A | 9/1964 | Mayfield et al. | 60/35.5 |
| 3,232,046 | A | 2/1966 | Meyer | 50/35.5 |
| 3,279,176 | A | 10/1966 | Boden | 60/202 |
| 3,746,870 | A | 7/1973 | Demarest | 250/227 |
| 3,960,473 | A | 6/1976 | Harris | 425/467 |
| 3,961,197 | A | 6/1976 | Dawson | 250/493 |
| 3,969,628 | A | 7/1976 | Roberts et al. | 250/402 |
| 4,042,848 | A | 8/1977 | Lee | 313/231.6 |
| 4,088,966 | A | 5/1978 | Samis | 313/231.5 |
| 4,143,275 | A | 3/1979 | Mallozzi et al. | 250/503 |
| 4,162,160 | A | 7/1979 | Witter | 75/246 |
| 4,203,393 | A | 5/1980 | Giardini | 123/30 |
| 4,223,279 | A | 9/1980 | Bradford et al. | 331/94.5 |
| 4,364,342 | A | 12/1982 | Asik | 123/143 |
| 4,369,758 | A | 1/1983 | Endo | 123/620 |
| 4,455,658 | A | 6/1984 | Sutter et al. | 372/38 |
| 4,504,964 | A | 3/1985 | Cartz et al. | 378/119 |
| 4,507,588 | A | 3/1985 | Asmussen et al. | 315/39 |
| 4,534,035 | A | 8/1985 | Long | 372/85 |
| 4,536,884 | A | 8/1985 | Weiss et al. | 378/119 |
| 4,538,291 | A | 8/1985 | Iwamatsu | 378/119 |
| 4,550,408 | A | 10/1985 | Karning et al. | 372/58 |
| 4,561,406 | A | 12/1985 | Ward | 123/536 |
| 4,596,030 | A | 6/1986 | Herziger et al. | 378/119 |
| 4,618,971 | A | 10/1986 | Weiss et al. | 378/34 |
| 4,626,193 | A | 12/1986 | Gann | 431/71 |
| 4,633,492 | A | 12/1986 | Weiss et al. | 378/119 |
| 4,635,282 | A | 1/1987 | Okada et al. | 378/34 |
| 4,751,723 | A | 6/1988 | Gupta et al. | 378/119 |
| 4,752,946 | A | 6/1988 | Gupta et al. | 378/119 |
| 4,774,914 | A | 10/1988 | Ward | 123/162 |
| 4,837,794 | A | 6/1989 | Riordan et al. | 378/119 |
| 4,891,820 | A | 1/1990 | Rando et al. | 372/93 |
| 4,928,020 | A | 5/1990 | Birx et al. | 307/106 |
| 4,959,840 | A | 9/1990 | Akins et al. | 372/57 |
| 5,005,180 | A | 4/1991 | Edelman et al. | 372/57 |
| 5,023,884 | A | 6/1991 | Akins et al. | 372/57 |
| 5,023,897 | A | 6/1991 | Neff et al. | 378/122 |
| 5,025,445 | A | 6/1991 | Anderson et al. | 372/20 |
| 5,025,446 | A | 6/1991 | Kuizenga | 372/21 |
| 5,027,076 | A | 6/1991 | Horsley et al. | 324/674 |
| 5,070,513 | A | 12/1991 | Letardi | 372/83 |
| 5,102,776 | A | 4/1992 | Hammer et al. | 430/311 |
| 5,126,638 | A | 6/1992 | Dethlefsen | 315/326 |
| 5,142,166 | A | 8/1992 | Birx | 307/419 |
| 5,171,360 | A | 12/1992 | Orme et al. | 75/331 |
| 5,175,755 | A | 12/1992 | Kumakhov | 378/34 |
| 5,189,678 | A | 2/1993 | Ball et al. | 372/28 |
| 5,226,948 | A | 7/1993 | Orme et al. | 75/331 |
| 5,259,593 | A | 11/1993 | Orme et al. | 266/78 |
| 5,313,481 | A | 5/1994 | Cook et al. | 372/37 |
| 5,315,611 | A | 5/1994 | Ball et al. | 372/56 |
| 5,319,695 | A | 6/1994 | Itoh et al. | 378/84 |
| 5,340,090 | A | 8/1994 | Orme et al. | 266/202 |
| 5,359,620 | A | 10/1994 | Akins | 372/58 |
| RE34,806 | E | 12/1994 | Cann | 427/446 |
| 5,411,224 | A | 5/1995 | Dearman et al. | 244/53 |
| 5,448,580 | A | 9/1995 | Birx et al. | 372/38 |
| 5,471,965 | A | 12/1995 | Kapich | 123/565 |
| 5,504,795 | A | 4/1996 | McGeoch | 378/119 |
| 5,729,562 | A | 3/1998 | Birx et al. | 372/38 |
| 5,763,930 | A | 6/1998 | Partlo | 250/504 |
| 5,852,621 | A | 12/1998 | Sandstrom | 372/25 |
| 5,856,991 | A | 1/1999 | Ershov | 372/57 |
| 5,863,017 | A | 1/1999 | Larson et al. | 248/176.1 |
| 5,866,871 | A | 2/1999 | Birx | 219/121 |
| 5,894,980 | A | 4/1999 | Orme-Marmarelis et al. | 228/33 |
| 5,894,985 | A | 4/1999 | Orme-Marmarelis et al. | 228/262 |
| 5,936,988 | A | 8/1999 | Partlo et al. | 372/38 |
| 5,938,102 | A | 8/1999 | Muntz et al. | 228/102 |
| 5,953,360 | A | 9/1999 | Vitruk et al. | 372/87 |
| 5,963,616 | A | 10/1999 | Silfvast et al. | 378/122 |
| 5,970,076 | A | 10/1999 | Hamada | 372/20 |
| 5,978,394 | A | 11/1999 | Newman et al. | 372/32 |
| 5,991,324 | A | 11/1999 | Knowles et al. | 372/57 |
| 6,005,879 | A | 12/1999 | Sandstrom et al. | 372/25 |
| 6,016,325 | A | 1/2000 | Ness et al. | 372/38 |
| 6,018,537 | A | 1/2000 | Hofmann et al. | 372/25 |
| 6,028,880 | A | 2/2000 | Carlesi et al. | 372/58 |
| 6,031,241 | A | 2/2000 | Silfvast et al. | 250/504 |
| 6,031,598 | A | 2/2000 | Tichenor et al. | 355/67 |
| 6,039,850 | A | 3/2000 | Schulz | 204/192.15 |
| 6,051,841 | A | 4/2000 | Partlo | 250/504 |
| 6,064,072 | A | 5/2000 | Partlo et al. | 250/504 |
| 6,067,311 | A | 5/2000 | Morton et al. | 372/57 |
| 6,094,448 | A | 7/2000 | Fomenkov et al. | 372/102 |
| 6,104,735 | A | 8/2000 | Webb | 372/37 |
| 6,128,323 | A | 10/2000 | Myers et al. | 372/38.1 |
| 6,151,346 | A | 11/2000 | Partlo et al. | 372/38 |
| 6,151,349 | A | 11/2000 | Gong et al. | 372/58 |
| 6,164,116 | A | 12/2000 | Rice et al. | 73/1.72 |
| 6,172,324 | B1 | 1/2001 | Birx | 219/121.57 |
| 6,186,192 | B1 | 2/2001 | Orme-Marmarelis et al. | 141/18 |
| 6,192,064 | B1 | 2/2001 | Algots et al. | 372/99 |
| 6,195,272 | B1 | 2/2001 | Pascente | 363/21 |
| 6,208,674 | B1 | 3/2001 | Webb et al. | 372/57 |
| 6,208,675 | B1 | 3/2001 | Webb | 372/58 |
| 6,219,368 | B1 | 4/2001 | Govorkov | 372/59 |
| 6,224,180 | B1 | 5/2001 | Pham-Van-Diep et al. | 347/2 |
| 6,228,512 | B1 | 5/2001 | Bajt et al. | 428/635 |
| 6,240,117 | B1 | 5/2001 | Gong et al. | 372/58 |
| 6,264,090 | B1 | 7/2001 | Muntz et al. | 228/33 |
| 6,276,589 | B1 | 8/2001 | Watts, Jr. et al. | 228/33 |
| 6,285,743 | B1 | 9/2001 | Kondo et al. | 378/119 |
| 6,304,630 | B1 | 10/2001 | Bisschops et al. | 378/119 |
| 6,307,913 | B1 | 10/2001 | Foster et al. | 378/34 |
| 6,317,448 | B1 | 11/2001 | Das et al. | 372/32 |
| 6,359,922 | B1 | 3/2002 | Partlo et al. | 372/58 |
| 6,370,174 | B1 | 4/2002 | Onkels et al. | 372/38.04 |
| 6,377,651 | B1 | 4/2002 | Richardson et al. | 378/34 |
| 6,381,257 | B1 | 4/2002 | Ershov et al. | 372/57 |
| 6,392,743 | B1 | 5/2002 | Zambon et al. | 355/69 |
| 6,396,900 | B1 | 5/2002 | Barbee, Jr. et al. | 378/84 |
| 6,404,784 | B2 | 6/2002 | Komine | 372/9 |
| 6,414,979 | B2 | 7/2002 | Ujazdowski et al. | 372/87 |
| 6,442,181 | B1 | 8/2002 | Oliver et al. | 372/25 |
| 6,449,086 | B1 | 9/2002 | Singh | 359/361 |
| 6,452,194 | B2 | 9/2002 | Bijkerk et al. | 250/492.2 |
| 6,452,199 | B1 | 9/2002 | Partlo et al. | 250/504 |
| 6,466,602 | B1 | 10/2002 | Fleurov et al. | 372/87 |
| 6,477,193 | B2 | 11/2002 | Oliver et al. | 372/58 |
| 6,491,737 | B2 | 12/2002 | Orme-Marmerelis et al. | 75/335 |
| 6,493,323 | B1 | 12/2002 | Dobrowolski et al. | 378/119 |
| 6,493,374 | B1 | 12/2002 | Fomenkov et al. | 372/102 |
| 6,520,402 | B2 | 2/2003 | Orme-Marmerelis et al. | 228/260 |
| 6,529,531 | B1 | 3/2003 | Everage et al. | 372/20 |
| 6,532,247 | B2 | 3/2003 | Spangler et al. | 372/61 |
| 6,535,531 | B1 | 3/2003 | Smith et al. | 372/25 |
| 6,538,737 | B2 | 3/2003 | Sandstrom et al. | 356/334 |
| 6,549,551 | B2 | 4/2003 | Ness et al. | 372/38.07 |
| 6,562,099 | B2 | 5/2003 | Orme-Marmerelis et al. | 75/335 |
| 6,566,667 | B1 | 5/2003 | Partlo et al. | 250/504 |
| 6,566,668 | B2 | 5/2003 | Rauch et al. | 250/504 |
| 6,567,450 | B2 | 5/2003 | Myers et al. | 372/55 |
| 6,567,499 | B2 | 5/2003 | McGeoch | 378/119 |
| 6,576,912 | B2 | 6/2003 | Visser et al. | 250/492.2 |
| 6,580,517 | B2 | 6/2003 | Lokai et al. | 356/519 |
| 6,584,132 | B2 | 6/2003 | Morton | 372/57 |
| 6,586,757 | B2 | 7/2003 | Melnychuk et al. | 250/504 |
| 6,590,922 | B2 | 7/2003 | Onkels et al. | 372/57 |
| 6,590,959 | B2 | 7/2003 | Kandaka et al. | 378/119 |
| 6,618,421 | B2 | 9/2003 | Das et al. | 372/55 |

| | | | | |
|---|---|---|---|---|
| 6,621,846 | B1 | 9/2003 | Sandstrom et al. | 372/57 |
| 6,625,191 | B2 | 9/2003 | Knowles et al. | 372/55 |
| 6,647,086 | B2 | 11/2003 | Amemiya et al. | 378/34 |
| 6,656,575 | B2 | 12/2003 | Bijkerk et al. | 428/212 |
| 6,671,294 | B2 | 12/2003 | Kroyan et al. | 372/20 |
| 6,711,233 | B2 | 3/2004 | Hertz et al. | 378/143 |
| 6,714,624 | B2 | 3/2004 | Fornaciari et al. | 378/119 |
| 6,721,340 | B1 | 4/2004 | Fomenkov et al. | 372/25 |
| 6,724,462 | B1 | 4/2004 | Singh et al. | 355/53 |
| 6,744,060 | B2 | 6/2004 | Ness et al. | 315/111.01 |
| 6,757,316 | B2 | 6/2004 | Newman et al. | 372/57 |
| 6,780,496 | B2 | 8/2004 | Bajt et al. | 425/216 |
| 6,782,031 | B1 | 8/2004 | Hofmann et al. | 372/90 |
| 6,795,474 | B2 | 9/2004 | Partlo et al. | 372/57 |
| 6,804,327 | B2 | 10/2004 | Schriever et al. | 378/119 |
| 6,815,700 | B2 | 11/2004 | Melnychuk et al. | 250/504 |
| 6,822,251 | B1 | 11/2004 | Arenberg et al. | 250/504 |
| 6,865,255 | B2 | 3/2005 | Richardson | 378/119 |
| 6,933,515 | B2 | 8/2005 | Hartlove et al. | 250/504 R |
| 7,372,056 | B2 * | 5/2008 | Bykanov et al. | 250/504 R |
| 2001/0006217 | A1 | 7/2001 | Bisschops | 250/493.1 |
| 2001/0055364 | A1 | 12/2001 | Kandaka et al. | 378/119 |
| 2002/0009176 | A1 | 1/2002 | Amemiya et al. | 378/34 |
| 2002/0048288 | A1 | 4/2002 | Kroyan et al. | 372/20 |
| 2002/0100882 | A1 | 8/2002 | Partlo et al. | 250/504 |
| 2002/0141536 | A1 | 10/2002 | Richardson | 378/119 |
| 2002/0168049 | A1 | 11/2002 | Schriever et al. | 378/119 |
| 2003/0068012 | A1 | 4/2003 | Ahmad et al. | 378/119 |
| 2003/0196512 | A1 | 10/2003 | Orme-Marmerelis et al. | 75/336 |
| 2003/0219056 | A1 | 11/2003 | Yager et al. | 372/57 |
| 2004/0047385 | A1 | 3/2004 | Knowles et al. | 372/55 |
| 2004/0264512 | A1 | 12/2004 | Hartlove et al. | 372/5 |
| 2005/0205810 | A1 | 9/2005 | Akins et al. | 250/504 R |
| 2006/0192155 | A1 | 8/2006 | Algots et al. | 250/504 R |

FOREIGN PATENT DOCUMENTS

| | | |
|---|---|---|
| JP | 03-173189 | 7/1991 |
| JP | 06-053594 | 2/1994 |
| JP | 09-219555 | 8/1997 |
| JP | 2000-058944 | 2/2000 |
| JP | 2000091096 A | 3/2000 |
| WO | WO 2004/104707 | 12/2004 |

OTHER PUBLICATIONS

Apruzese, J.P., "X-Ray Laser Research Using Z Pinches," *Am. Inst. of Phys.* 399-403, (1994).

Bal et al., "Optimizing multiplayer coatings for Extreme UV projection systems," Faculty of Applied Sciences, Delft University of Technology, 2004.

Bollanti, et al., "Compact Three Electrodes Excimer Laser IANUS for a POPA Optical System," *SPIE Proc.* (2206)144-153, (1994).

Bollanti, et al., "Ianus, the three-electrode excimer laser," *App. Phys. B (Lasers & Optics)* 66(4):401-406, (1998).

Braun, et al., "Multi-component EUV Multilayer Mirrors," *Proc. SPIE*, 5037:2-13, (2003).

Choi, et al., "A $10^{13}$ A/s High Energy Density Micro Discharge Radiation Source," *B. Radiation Characteristics*, p. 287-290, 1999.

Choi, et al., "Fast pulsed hollow cathode capillary discharge device," *Rev. of Sci. Instrum.* 69(9):3118-3122 (1998).

Choi et al., Temporal development of hard and soft x-ray emission from a gas-puff Z pinch, *Rev. Sci. Instrum.* 57(8), pp. 2162-2164 (Aug. 1986).

Coutts et al., "High average power blue generation from a copper vapour laser pumped titanium sapphire laser", Journal of Modern Optics, vol. 45, No. 6, p. 1185-1197 (1998).

Eckhardt, et al., "Influence of doping on the bulk diffusion of Li into Si(100)," *Surface Science* 319 (1994) 219-223.

Eichler, et al., "Phase conjugation for realizing lasers with diffraction limited beam quality and high average power," Techninische Universitat Berlin, Optisches Institut, (Jun. 1998).

Fedosejevs et al., "Subnanosecond pulses from a KrF Laser pumped $SF_6$ Brillouin Amplifier", *IEEE J. QE* 21, 1558-1562 (1985).

Feigl, et al., "Heat Resistance of EUV Multilayer Mirrors for Long-time Applications," *Microelectric Engineering*, 57-58:3-8, (2001).

Fomenkov, et al., "Characterization of a 13.5nm Source for EUV Lithography based on a Dense Plasma Focus and Lithium Emission," Sematech Intl. Workshop on EUV Lithography (Oct. 1999).

Giordano et al., "Magnetic pulse compressor for prepulse discharge in spiker-sustainer excitati technique for XeC1 lasers," *Rev. Sci. Instrum* 65(8), pp. 2475-2481 (Aug. 1994).

Hansson, et al., "Xenon liquid jet laser-plasma source for EUV lithography," Emerging Lithographic Technologies IV, *Proc. of SPIE*, vol. 3997:729-732 (2000).

Hercher, "Tunable single mode operation of gas lasers using intracavity tilted etalons," Applied Optics, vol. 8, No. 6, Jun. 1969, pp. 1103-1106.

Jahn, Physics of Electric Propulsion, McGraw-Hill Book Company, (Series in Missile and Space U.S.A.), Chap. 9, "Unsteady Electromagnetic Acceleration," p. 257 (1968).

Jiang, et al., "Compact multimode pumped erbium-doped phosphate fiber amplifiers," *Optical Engineering*, vol. 42, Issue 10, pp. 2817-2820 (Oct. 2003).

Kato, Yasuo, "Electrode Lifetimes in a Plasma Focus Soft X-Ray Source," *J. Appl. Phys.* (33) Pt. 1, No. 8:4742-4744 (1991).

Kato, et al., "Plasma focus x-ray source for lithography," *Am. Vac. Sci. Tech. B.*, 6(1): 195-198 (1988).

Kjornrattanawanich, Ph.D. Dissertation, U.S. Department of Energy, Lawrence Livermore National Laboratory, Sep. 1, 2002.

Kloidt et al., "Enhancement of the reflectivity of Mo/Si multilayer x-ray mirrors by thermal treatment," *Appl. Phys. Lett.* 58(23), 2601-2603 (1991).

Kuwahara et al., "Short-pulse generation by saturated KrF laser amplification of a steep Stokes pulse produced by two-step stimulated Brillouin scattering", *J. Opt. Soc. Am.* B 17, 1943-1947 (2000).

Lange, Michael R., et al., "High gain coefficient phosphate glass fiber amplifier," NFOEC 2003, paper No. 126.

Lebert, et al., "Soft x-ray emission of laser-produced plasmas using a low-debris cryogenic nitrogen target," *J. Appl. Phys.*, 84(6):3419-3421 (1998).

Lebert, et al., "A gas discharged based radiation source for EUV-lithography," Intl. Conf. Micro and Nano-Engineering 98 (Sep. 22-24, 1998) Leuven, Belgium.

Lebert, et al., "Investigation of pinch plasmas with plasma parameters promising ASE," Inst. Phys. Conf. Ser No. 125: Section 9, pp. 411-415 (1992) Schiersee, Germany.

Lebert, et al., "Comparison of laser produced and gas discharge based EUV sources for different applications," Intl. Conf. Micro- and Nano-Engineering 98 (Sep. 22-24, 1998) Leuven, Belgium.

Lee, Ja H., "Production of dense plasmas in hypocycloidal pinch apparatus," *The Phys. Of Fluids*, 20(2):313-321 (1977).

Lewis, Ciaran L.S., "Status of Collision-Pumped X-ray Lasers," *Am. Inst. Phys.* pp. 9-16 (1994).

Lowe, "Gas plasmas yield X-rays for Lithography," *Electronics*, pp. 40-41 (Jan. 27, 1982).

Malmquist, et al., "Liquid-jet target for laser-plasma soft x-ray generation," *Am. Inst. Phys.* 67(12):4150-4153 (1996).

Maruyama et al., Characteristics of high-power excimer laser master oscillator power amplifier system for dye laser pumping, Optics Communications, vol. 87, No. 3 p. 105-108 (1992).

Mather, "Formation of a High-Density Deuterium Plasma Focus," *Physics of Fluids*, 8(2), 366-377 (Feb. 1965).

Mather, et al., "Stability of the Dense Plasma Focus," *Phys. of Fluids*, 12(11):2343-2347 (1969).

Matthews and Cooper, "Plasma sources for x-ray lithography," *SPIE, vol. 333 Submicron Lithography*, pp. 136-139 (1982).

Mayo, et al., "A magnetized coaxial source facility for the generation of energetic plasma flows," *Sci. Technol.* vol. 4:pp.47-55 (1994).

Mayo, et al., "Initial Results on high enthalpy plasma generation in a magnetized coaxial source," *Fusion Tech* vol. 26:1221-1225 (1994).

Mitsuyama, et al., "Compatibility of insulating ceramic materials with liquid breeders," *Fusion Eng. and Design* 39-40 (1998) 811-817.

Montcalm et al., "Mo/Y multiplayer mirrors for the 8-12-nm wavelength region," *Optics Letters*, 19(15): 1173-1175 (Aug. 1, 1994).

Montcalm et al., "In situ reflectance measurements of soft-s-ray/extreme-ultraviolet Mo/Y multiplayer mirrors," *Optics Letters* 20(12): 1450-1452 (Jun. 15, 1995).

Nilsen et al., "Mo: Y multiplayer mirror technology utilized to image the near-field output of a Ni-like Sn laser at 11.9 nm," *Optics Letters*, 28(22) 2249-2251 (Nov. 15, 2003).

Nilsen, et al., "Analysis of resonantly photopumped Na-Ne x-ray-laser scheme," *Am Phys. Soc.* 44(7):4591-4597 (1991).

H. Nishioka et al., "UV saturable absorber for short-pulse KrF laser systems", *Opt. Lett.* 14, 692-694 (1989).

Orme, et al., "Electrostatic charging and deflection of nonconventional droplet streams formed from capillary stream breakup," *Physics of Fluids*, 12(9):2224-2235, (Sep. 2000).

Orme, et al., "Charged Molten Metal Droplet Deposition As a Direct Write Technology", MRS 2000 Spring Meeting, San Francisco, (Apr. 2000).

Pant, et al., "Behavior of expanding laser produced plasma in a magnetic field," *Physica Sripta*, T75:104-111, (1998).

Partlo, et al., "EUV (13.5nm) Light Generation Using a Dense Plasma Focus Device," *SPIE Proc. On Emerging Lithographic Technologies III*, vol. 3676, 846-858 (Mar. 1999).

Pearlman et al., "X-ray lithography using a pulsed plasma source," *J. Vac. Sci. Technol.*, pp. 1190-1193 (Nov./Dec. 1981).

Pint et al., "High temperature compatibility issues for fusion reactor structural materials," Metals and Ceramics Division, Oak Ridge National Laboratory, P.O. Box 2008, Oak Ridge, TN 37831-6156, 2003.

Porter, et al., "Demonstration of Population Inversion by Resonant Photopumping in a Neon Gas Cell Irradiated by a Sodium Z Pinch," *Phys. Rev. Let.*, 68(6):796-799, (Feb. 1992).

Price, Robert H., "X-Ray Microscopy using Grazing Incidence Reflection Optics," *Am. Inst. Phys.* , pp. 189-199, (1981).

Qi, et al., "Fluorescence in Mg IX emission at 48.340 Åfrom Mg pinch plasmas photopumped by A1 XI line radiation at 48.338 Å," *The Am. Phys. Soc.*, 47(3):2253-2263 (Mar. 1993).

Sae-Lao et al., "Performance of normal-incidence molybdenum-yttrium multilayer-coated diffraction grating at a wavelength of 9 nm," *Applied Optics*, 41(13):2394-1400 (May 1 2002).

Sae-Lao et al., "Molybdenum-strontium multiplayer mirrors for the 8-12-nm extreme-ultraviolet wavelength region," *Optics Letters*, 26(7):468-470, (Apr. 1, 2001).

Sae-Lao et al., "Normal-incidence multiplayer mirrors for the 8-12 nm wavelength region," Information Science and Technology, Lawrence Livermore National Laboratory, 2003.

Sae-Lao et al., "Measurements of the refractive index of ytrrium in the 50-1300-eV energy region," *Applied Optics* , 41(34):7309-7316 (Dec. 1, 2002).

Scheuer, et al., "A Magnetically-Nozzled, Quasi-Steady, Multimegawatt, Coaxial Plasma Thruster," *IEEE-Transactions on Plasma Science*, 22(6) (Dec. 1994).

S. Schiemann et al., "Efficient temporal compression of coherent nanosecond pulses in a compact SBS generator-amplifier setup", *IEEE J. QE* 33, 358-366 (1997).

Schriever, et al., "Laser-produced lithium plasma as a narrow-band extended ultraviolet radiation source for photoelectron spectroscopy," *App. Optics*, 37(7):1243-1248, (Mar. 1998).

Schriever, et al., "Narrowband laser produced extreme ultraviolet sources adapted to silicon/molybdenum multilayer optics," *J. of App. Phys.*, 83(9):4566-4571, (May 1998).

Sharafat et al., Coolant Structural Materials Compatibility, Joint APEX Electronic Meeting, UCLA, (Mar. 24, 2000).

Shiloh et al., "Z Pinch of a Gas Jet," *Physical Review Lett.*, 40(8), pp. 515-518 (Feb. 20, 1978).

Silfvast, et al., "High-power plasma discharge source at 13.5 nm and 11.4 nm for EUV lithography," *SPIE*, vol. 3676:272-275, (Mar. 1999).

Silfvast, et al., "Lithium hydride capillary discharge creates x-ray plasma at 13.5 nanometers," *Laser Focus World*, p. 13. (Mar. 1997).

Singh et al., "Improved Theoretical Reflectivities of Extreme Ultraviolet Mirrors," Optics Research Group, Faculty of Applied Sciences, Delft University of Technology, 2000.

Singh et al., "Design of multiplayer extreme-ultraviolet mirrors for enhanced reflectivity," *Applied Optics*, 39(13):2189-2197 (May 1 2000).

Soufli, et al., "Absolute photoabsorption measurements of molybdenum in the range 60-930 eV for optical constant determination," *Applied Optics* 37(10): 1713-1719 (Apr. 1, 1998).

Srivastava et al., "High-temperature studies on Mo-Si multilayers using transmission electron microscope," *Current Science*, 83 (8):997-1000 (Oct. 25, 2002).

Stallings et al., "Imploding argon plasma experiments," *Appl. Phys. Lett.*, 35(7), pp. 524-526 (Oct. 1, 1979).

Tada et al., "1-pm spectrally narrowed compact ArF excimer laser for microlithography", Laser and Electro-Optics, CLEO '96, CThG4, p. 374 (1996).

Takahashi, E., et al., "KrF laser picosecond pulse source by stimulated scattering processes", *Opt. Commun.*215, 163-167 (2003).

Takahashi, E., et al., "High-intensity short KrF laser-pulse generation by saturated amplification of truncated leading-edge pulse", *Opt. Commun.* 185, 431-437 (2000).

Takenaka, et al., "Heat resistance of Mo/Si, $MoSi_2$/Si, and $Mo_5Si_3$/Si multiplayer soft x-ray mirrors," *J. Appl. Phys.* 78(9) 5227-5230 (Nov. 1, 1995).

Tillack, et al., "Magnetic Confinement of an Expanding Laser-Produced Plasma", UC San Diego, Center for Energy Research, UCSD Report & Abramova—Tornado Trap, 2003.

Willhein, et al., "A slit grating spectrograph for quantitative soft x-ray spectroscopy," *Am. Inst. OfPhys. Rev. of Sci. Instrum.*, 70(3):1694-1699, (Mar. 1999).

Wu, et al., "The vacuum Spark and Spherical Pinch X-ray/EUV Point Sources," *SPIE, Conf. On Emerging Tech. III*, Santa Clara, CA, vol. 3676:410-420, (Mar. 1999).

Yusheng et al., "Recent progress of "Heaven-One" high power KrF excimer laser system", Laser and Electro-Optics, CLEO '96, CThG4, p. 374 (1996).

Zornbeck, M.V., "Astrophysical Observations with High Resolution X-ray Telescope," *Am. Inst. OfPhys.*, pp. 200-209, (1981).

* cited by examiner

LPP EUV PLASMA SOURCE MATERIAL TARGET DELIVERY SYSTEM

RELATED APPLICATIONS

The present application is a Continuation of U.S. application Ser. No. 11/174,443, entitled LPP EUV PLASMA SOURCE MATERIAL TARGET DELIVERY SYSTEM, filed Jun. 29, 2005, The present application is related to co-pending U.S. application Ser. No. 11/021,261, entitled EUV LIGHT SOURCE OPTICAL ELEMENTS, filed on Dec. 22, 2004, and Ser. No. 10/979,945, entitled EUV COLLECTOR DEBRIS MANAGEMENT, filed on Nov. 1, 2004, Ser. No. 10/979,919, entitled LPP EUV LIGHT SOURCE, filed on Nov. 1, 2004, Ser. No. 10/900,839, entitled EUV Light Source, filed on Jul. 27, 2004, Ser. No. 10/798,740, filed on Mar. 10, 2004, entitled COLLECTOR FOR EUV LIGHT SOURCE, Ser. No. 11/067,124, filed Feb. 25, 2005, entitled METHOD AND APPARATUS FOR EUV PLASMA SOURCE TARGET DELIVERY, Ser. No. 10/803,526, filed on Mar. 17, 2004, entitled, A HIGH REPETITION RATE LASER PRODUCED PLASMA EUV LIGHT SOURCE, Ser. No. 10/409,254, entitled EXTREME ULTRAVIOLET LIGHT SOURCE, filed on Apr. 8, 2003, and Ser. No. 10/798,740, entitled COLLECTOR FOR EUV LIGHT SOURCE, filed on Mar. 10, 2004, and Ser. No. 10/615,321, entitled A DENSE PLASMA FOCUS RADIATION SOURCE, filed on Jul. 7, 2003, and Ser. No. 10/742,233, entitled DISCHARGE PRODUCED PLASMA EUV LIGHT SOURCE, filed on Dec. 18, 2003, and Ser. No. 10/442,544, entitled A DENSE PLASMA FOCUS RADIATION SOURCE, filed on May 21, 2003, all co-pending and assigned to the common assignee of the present application, the disclosures of each of which are hereby incorporated by reference.

FIELD OF THE INVENTION

The present invention related to Extreme ultraviolet ("EUV") light source systems.

BACKGROUND OF THE INVENTION

Laser produced plasma ("LPP") extreme ultraviolet light ("EUV"), e.g., at wavelengths below about 50 nm, using plasma source material targets in the form of a jet or droplet forming jet or droplets on demand comprising plasma formation material, e.g., lithium, tin, xenon, in pure form or alloy form (e.g., an alloy that is a liquid at desired temperatures) or mixed or dispersed with another material, e.g., a liquid. Delivering this target material to a desired plasma initiation site, e.g., at a focus of a collection optical element presents certain timing and control problems that applicants propose to address according to aspects of embodiments of the present invention.

SUMMARY OF THE INVENTION

An EUV light generation system and method is disclosed that may comprise a droplet generator producing plasma source material target droplets traveling toward the vicinity of a plasma source material target irradiation site; a drive laser; a drive laser focusing optical element having a first range of operating center wavelengths; a droplet detection radiation source having a second range of operating center wavelengths; a drive laser steering element comprising a material that is highly reflective within at least some part of the first range of wavelengths and highly transmissive within at least some part of the second range of center wavelengths; a droplet detection radiation aiming mechanism directing the droplet detection radiation through the drive laser steering element and the lens to focus at a selected droplet detection position intermediate the droplet generator and the irradiation site. The apparatus and method may further comprise a droplet detection mechanism that may comprise a droplet detection radiation detector positioned to detect droplet detection radiation reflected from a plasma source material droplet. The droplet detection radiation source may comprise a solid state low energy laser. The droplet detection radiation aiming mechanism may comprise a mechanism selecting the angle of incidence of the droplet detection radiation on the drive laser steering element. The apparatus and method may comprise a droplet detection radiation detector comprising a radiation detector sensitive to light in the second range of center wavelengths and not sensitive to radiation within the second range of center wavelengths. The droplet detection radiation may be focused to a point at or near the selected droplet detection position such that the droplet detection radiation reflects from a respective plasma source material target at the selected droplet detection position. The EUV plasma source material target delivery system may comprise a plasma source material target formation mechanism which may comprise a plasma source target droplet formation mechanism comprising a flow passageway and an output orifice; a stream control mechanism comprising an energy imparting mechanism imparting stream formation control energy to the plasma source material droplet formation mechanism to at least in part control a characteristic of the formed droplet stream; and, an imparted energy sensing mechanism sensing the energy imparted to the stream control mechanism and providing an imparted energy error signal. The target steering mechanism feedback signal may represent a difference between an actual energy imparted to the stream control mechanism and an actuation signal imparted to the energy imparting mechanism. The flow passageway may comprise a capillary tube.

DETAILED DESCRIPTION OF PREFERRED EMBODIMENTS

Figure 1:
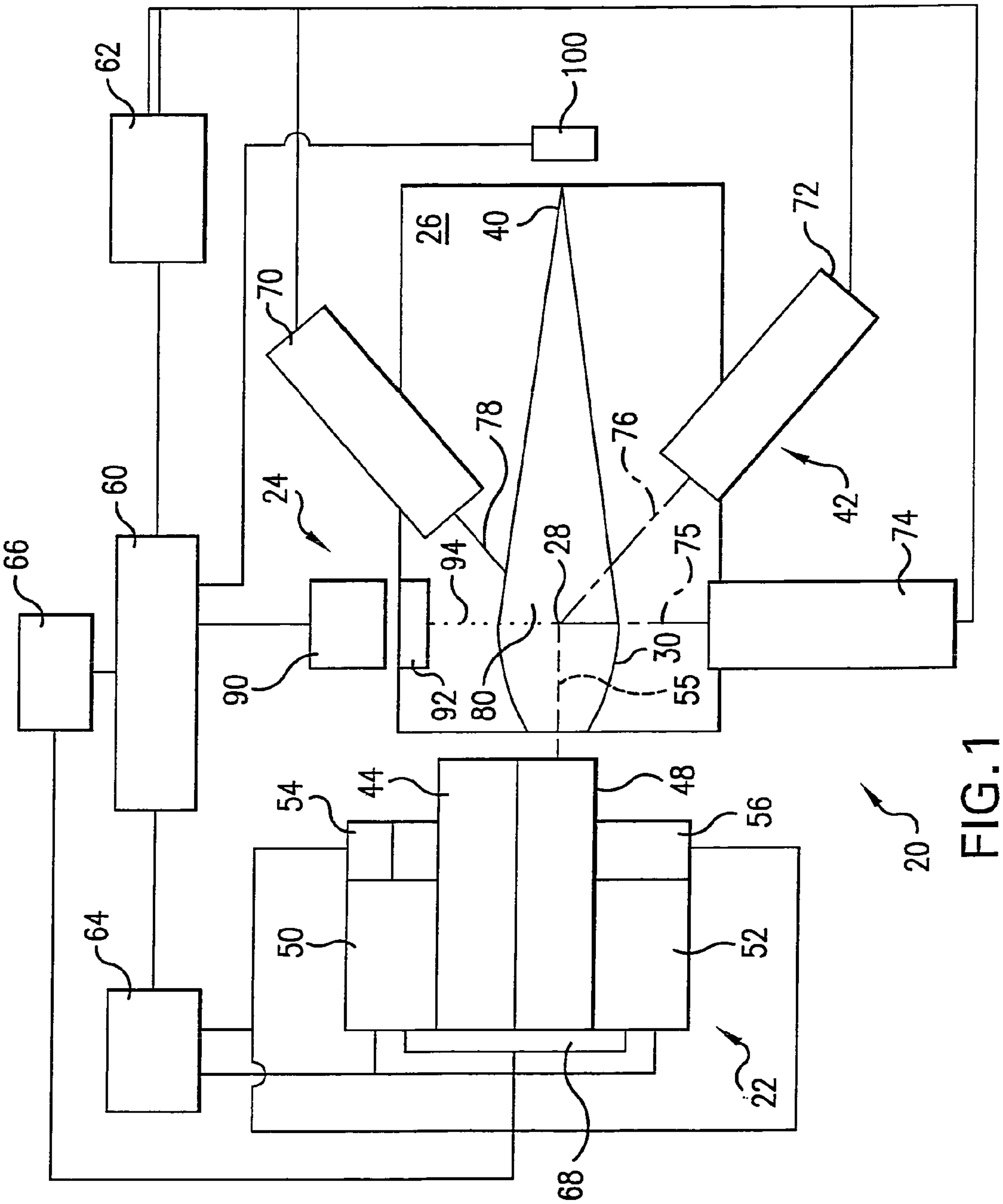
FIG. 1 shows schematically and in block diagram form an exemplary extreme ultraviolet ("EUV") light source (otherwise known as a soft X-ray light source) according to aspects of an embodiment of the present invention.

Turning now to FIG. 1 there is shown a schematic view of an overall broad conception for an EUV light source, e.g., a laser produced plasma EUV light source 20 according to an aspect of the present invention. The light source 20 may contain a pulsed laser system 22, e.g., a gas discharge excimer or molecular fluorine laser operating at high power and high pulse repetition rate and may be a MOPA configured laser system, e.g., as shown in U.S. Pat. Nos. 6,625,191, 6,549,551, and 6,567,450. The light source 20 may also include a target delivery system 24, e.g., delivering targets in the form of liquid droplets, solid particles or solid particles contained within liquid droplets. The targets may be delivered by the target delivery system 24, e.g., into the interior of a chamber 26 to an irradiation site 28, otherwise known as an ignition site or the sight of the fire ball, which is where irradiation by the laser causes the plasma to form from the target material. Embodiments of the target delivery system 24 are described in more detail below.

Laser pulses delivered from the pulsed laser system 22 along a laser optical axis 55 through a window (not shown) in the chamber 26 to the irradiation site, suitably focused, as discussed in more detail below in coordination with the arrival of a target produced by the target delivery system 24 to create an x-ray releasing plasma, having certain characteristics, including wavelength of the x-ray light produced, type and amount of debris released from the plasma during or after ignition, according to the material of the target.

The light source may also include a collector 30, e.g., a reflector, e.g., in the form of a truncated ellipse, with an aperture for the laser light to enter to the irradiation site 28. Embodiments of the collector system are described in more detail below. The collector 30 may be, e.g., an elliptical mirror that has a first focus at the plasma initiation site 28 and a second focus at the so-called intermediate point 40 (also called the intermediate focus 40) where the EUV light is output from the light source and input to, e.g., an integrated circuit lithography tool (not shown). The system 20 may also include a target position detection system 42. The pulsed system 22 may include, e.g., a master oscillator-power amplifier ("MOPA") configured dual chambered gas discharge laser system having, e.g., an oscillator laser system 44 and an amplifier laser system 48, with, e.g., a magnetic reactor-switched pulse compression and timing circuit 50 for the oscillator laser system 44 and a magnetic reactor-switched pulse compression and timing circuit 52 for the amplifier laser system 48, along with a pulse power timing monitoring system 54 for the oscillator laser system 44 and a pulse power timing monitoring system 56 for the amplifier laser system 48. The system 20 may also include an EUV light source controller system 60, which may also include, e.g., a target position detection feedback system 62 and a firing control system 64, along with, e.g., a laser beam positioning system 66.

The target position detection system 42 may include a plurality of droplet imagers 70, 72 and 74 that provide input relative to the position of a target droplet, e.g., relative to the plasma initiation site and provide these inputs to the target position detection feedback system, which can, e.g., compute a target position and trajectory, from which a target error can be computed, if not on a droplet by droplet basis then on average, which is then provided as an input to the system controller 60, which can, e.g., provide a laser position and direction correction signal, e.g., to the laser beam positioning system 66 that the laser beam positioning system can use, e.g., to control the position and direction of the laser position and direction changer 68, e.g., to change the focus point of the laser beam to a different ignition point 28.

The imager 72 may, e.g., be aimed along an imaging line 75, e.g., aligned with a desired trajectory path of a target droplet 94 from the target delivery mechanism 92 to the desired plasma initiation site 28 and the imagers 74 and 76 may, e.g., be aimed along intersecting imaging lines 76 and 78 that intersect, e.g., alone the desired trajectory path at some point 80 along the path before the desired ignition site 28.

The target delivery control system 90, in response to a signal from the system controller 60 may, e.g., modify the release point of the target droplets 94 as released by the target delivery mechanism 92 to correct for errors in the target droplets arriving at the desired plasma initiation site 28.

An EUV light source detector 100 at or near the intermediate focus 40 may also provide feedback to the system controller 60 that can be, e.g., indicative of the errors in such things as the timing and focus of the laser pulses to properly intercept the target droplets in the right place and time for effective and efficient LPP EUV light production.

Figure 2:
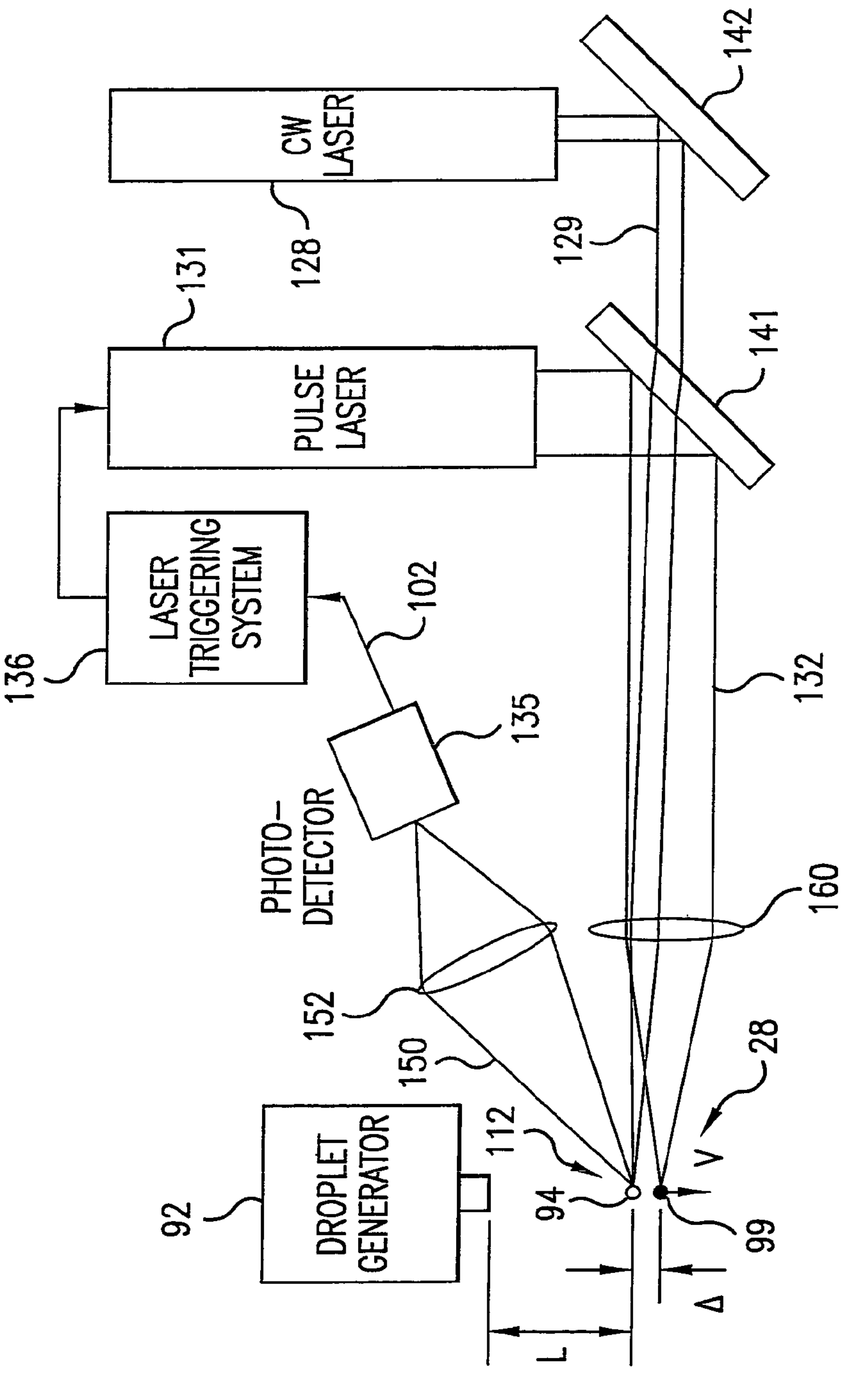
FIG. 2 shows a schematic block diagram of a plasma source material target tracking system according to aspects of an embodiment of the present invention.

Turning now to FIG. 2 there is shown in schematic block diagram form a plasma source material target tracking system according to aspects of an embodiment of the present invention for tracking plasma source material targets, e.g., in the form of droplets of plasma source material to be irradiated by a laser beam to form an EUV generating plasma. The combination of high pulse rate laser irradiation from one or more laser produced plasma EUV drive laser pulsed lasers and droplet delivery at, e.g., several tens of kHz of droplets, can create certain problems for accurately triggering the laser(s) due to, e.g., jitter of the droplet velocity and/or the creation of satellite droplets, which may cause false triggering of the laser without the proper targeting to an actual target droplet, i.e., targeting a satellite droplet of a droplet out of many in a string of droplets. For example, where one or more droplets are meant to shield upstream droplets from the plasma formed using a preceding droplet, the wrong droplet in the string may be targeted. Applicants propose certain solutions to these types of problems, e.g., by using an improved optical scheme for the laser triggering which can improve the stability of radiation output of a target-droplet-based LPP EUV light source.

As can be seen in FIG. 2 a schematic block diagram of the optical targeting system is illustrated by way of example. Droplets 94 can be generated by the droplet generator 92. An optical intensity signal 102 may be generated by a droplet imager, e.g., the imager 70 shown schematically in FIG. 1, which is represented more specifically by a photo-detector 135 in FIG. 2. The photo-detector may detect, e.g., a reflection of light from, e.g., a detection light source, e.g., a low power laser light source 128, which may be, e.g., a continuous wave ("CW") solid state laser, or a HeNe laser. This reflection can occur, e.g., when a droplet 94 intersects a focused CW laser radiation beam 129 from the CW laser 128. The photo-detector 135 may be positioned such that the reflected light from the droplet 94 is focused on the photo-detector 135, e.g., with or without a lens 134. The signal 102 from the photo-detector 135 can, e.g., trigger the main laser drive controller, e.g., 60 as illustrated schematically in FIG. 1 and more specifically as 136 in FIG. 2.

Initially laser radiation 132 from the main laser 131 (which may be one of two or more main drive lasers) may be co-aligned with laser radiation 129 from CW laser 128 by using, for example, 45 degrees dichroic mirrors 141 and 142.

It will be understood that there is a certain total delay time $\tau_L$ between the laser trigger, e.g., in response to the controller 136 receiving the signal 102 from the photo-detector, and the generation of a laser trigger signal to the laser, e.g., a solid state YAG laser, and for the laser then to generate a pulse of laser radiation, e.g., about 200 μs for a YAG laser. Furthermore, if the drive laser is a multistage laser system, e.g., a master oscillator-power amplifier or power oscillator ("MOPA" or "MOPO"), with, e.g., a solid state YAG laser as the MO and a gas discharge laser, e.g., an excimer or molecular fluorine or $CO_2$ laser as the PA or PO, there is a delay from the generation of the of the seed laser pulse in the master oscillator portion of the laser system and the output of an amplified laser pulse from the amplifier section of the laser, usually on the order of tens of ns. This total error time $\tau_L$, depending on the specific laser(s) used and the specific configuration, may be easily determined as will be understood by those skilled in the art.

Thus the focus of CW beam 129 according to aspects of an embodiment of the present invention can be made to be separated from the focus of the main laser(s) 131 (plasma source material droplet irradiation site 28) with the distance of $\Delta l \approx v^* . \tau_L$, where v is average velocity of the droplets 94. The system may be set up so that the droplets 94 intersect the CW beam 129 prior to the main laser(s) beam(s) 132. This separation may be, e.g., 200-400 μm for the droplet velocities of 1-2 m/s, e.g., in the case of a single stage solid state YAG drive laser and, e.g., a steady stream of a droplet-on-demand droplet generator 92.

According to aspects of an embodiment of the present invention applicants propose turning the mirror 142 to provide for this selected amount of separation between the triggering detection site 112 and the plasma source material irradiation site 28. Such a small separation with respect to L (output of the droplet generator 94 to plasma initiation site 28) improves proper targeting and, thus EUV output. For example, for L=50 mm and droplet velocity 10 m/sec, e.g., a 10% of droplet to droplet velocity variation can give droplet position jitter of about 0.5 mm, which may be several times large than the droplet diameter. In the case of 500 μm separation this jitter is reduced to 5 μm.

The reflected light 150 from the target droplet 94 intersected by the CW laser beam 129, focused through the same focusing lens 160 as the drive laser light beam 132 may be focused on the photo-detector 135 by another focusing lens 152. Focusing the CW droplet detection light beam 129 through the same focusing lens 160 as the drive laser beam 132 can, e.g., result in a self-aligned beam steering mechanism and one which uses the same laser input window, thereby facilitating the arrangement of the window protection and cleaning, i.e., one less window is needed.

According to aspects of an embodiment of the present invention using a focused CW radiation can reduce the possibility of triggering from the satellite droplets and also increase the triggering reliability due to increased signal intensity as compared to the two serial CW curtains, which were proposed for optical triggering. Applicants in operating prototype liquid metal droplet generators for producing plasma source material target droplets have found that some means of correcting for drift/changes in a droplet generator actuator, e.g., an actuator using PZT properties and energy coupling to displace some portion or all of a droplet generator, e.g., the capillary along with a nozzle at the discharge end of the capillary and/or an output orifice of the capillary or the nozzle, over time. Correcting for such modifications over time can be used, according to aspects of an embodiment of the present invention to attain stable long-term operation.

By, e.g., optically sensing the droplet formation process, e.g., only changes large enough to cause droplet stability problems may be detected, e.g., by detecting a displacement error for individual droplets or an average over a selected number of droplets. Further such detection may not always provide from such droplet stability data what parameter(s) to change, and in what fashion to correct for the droplet instability. For example, it could be an error in, e.g., the x-y position of the output orifice, the angular positioning of the capillary, the displacement force applied to the plasma source material liquid inside the droplet generator for droplet/liquid jet formation, the temperature of the plasma formation material, etc. that is resulting in the droplet stability problems.

According to aspects of an embodiment of the present invention a closed loop control system may be utilized to maintain stable target droplet formation and delivery operation at a fixed frequency, e.g., by monitoring the actual displacement/vibration or the like of the liquid capillary tube or orifice in comparison to an actuator signal applied to an actuator to apply cause such displacement/vibration. In such a control system the dominant control factor would not be the PZT drive voltage but the energy transferred to at least some portion of the droplet generating mechanism and, the resulting induced movement/vibration, etc. As such, the use of this parameter as feedback when controlling, e.g., the actuator drive voltage can be a more correlated and stable measure of the changes needed to induce proper droplet formation and delivery. Also, monitoring the drive voltage/induced motion relationship (including off frequency motion etc.) can be an effective way to detect early failure symptoms, e.g., by sensing differences between an applied actuator signal and a resultant movement/vibration outside of some selected threshold difference.

Figure 3:
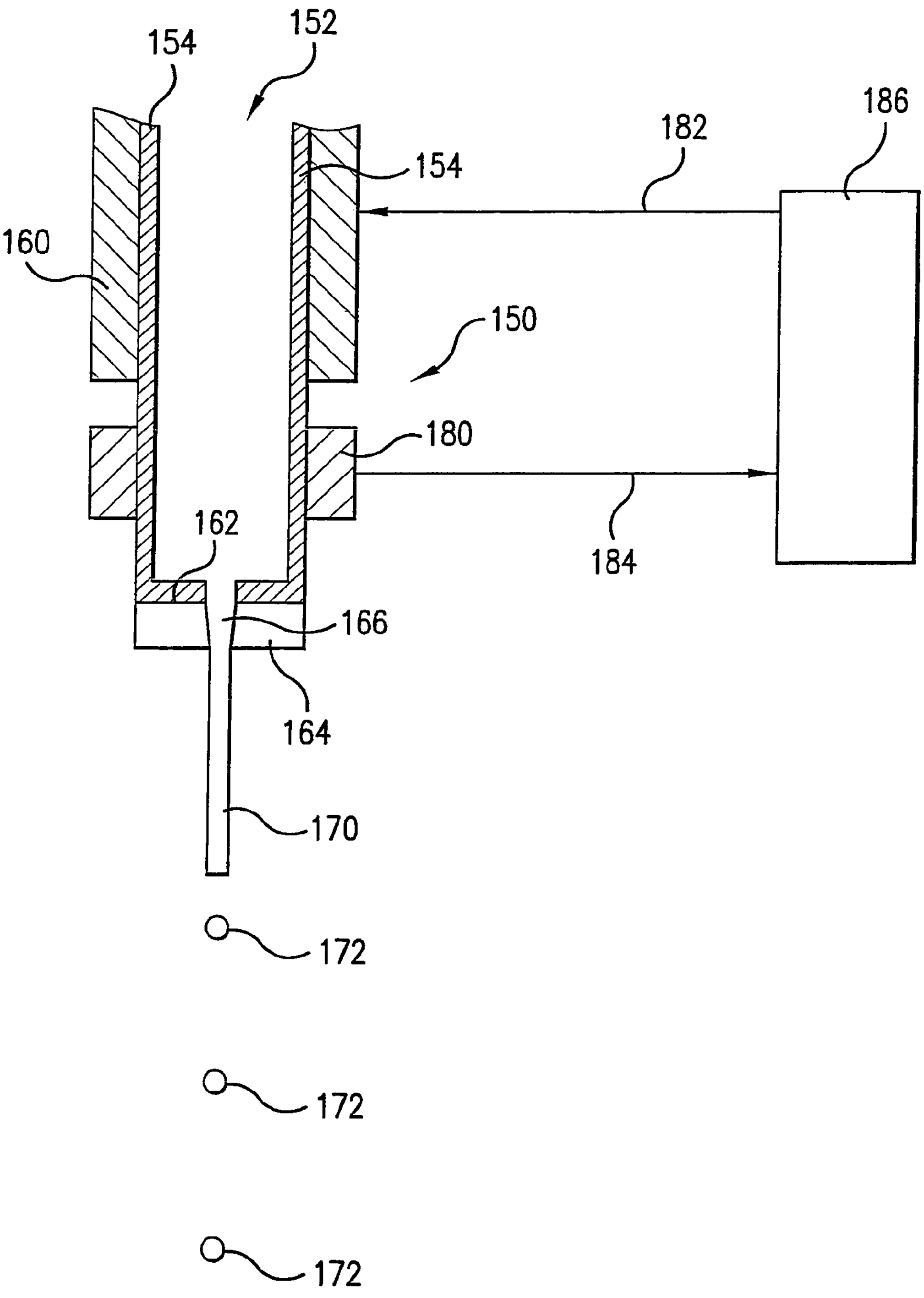
FIG. 3 shows partly schematically a cross-sectional view of a target droplet delivery system according to aspects of an embodiment of the present invention.

A PZT drive voltage feedback system utilizing the actual motion/vibration imparted by the PZT as a feedback signal, according to aspects of an embodiment of the present invention is illustrated by way of Example in FIG. 3. The sensor could be another PZT, a laser based interferometric sensor, a capacitive sensor or other appropriate sensor. Turning now to FIG. 3 there is shown, partly in cross section and partly schematically, a portion of an EUV plasma source material target delivery system 150, which may comprise a capillary 152 having a capillary wall 154 that may terminate, e.g., in a bottom wall 162, and be attached thereto by, e.g., being welded in place. The capillary wall 154 may be encased in part by an actuator 160, which may, e.g., be an actuatable material that changes size or shape under the application of an actuating field, e.g., an electrical field, a magnetic field or an acoustic field, e.g., a piezoelectric material. It will be understood that the material may simply try to change shape or size thus applying desired stress or strain to an adjacent material or structure, e.g., the capillary wall 154.

The system 150 may also comprise an orifice plate 164, including a plasma source material liquid stream exit orifice 166 at the discharge end of the capillary tube 152, which may or may not constitute or be combined with some form of nozzle. The output orifice plate 164 may also be sealed to the plasma source material droplet formation system by an o-ring seal 168.

It will be understood that in operation the plasma source material droplet formation system 150 may form, e.g., in a continuous droplet delivery mode, a stream 170 of liquid that exits the orifice 166 and eventually breaks up into droplets 172, depending on a number of factors, among them the type of plasma source material being used to form the droplets 172, the exit velocity and size of the stream 170, etc. The system 150 may induce this formation of the exit stream 170, e.g., by applying pressure to the plasma source material in liquid form, e.g., in a reservoir (not shown) up stream of the capillary tube 152. The actuator 160 may serve to impart some droplet formation influencing energy to the plasma source material liquid, e.g., prior to exit from the exit orifice 166, e.g., by vibrating or squeezing the capillary tube 152. In this manner, e.g., the velocity of the exit stream and/or other properties of the exit stream that influence droplet 172 formation, velocity, spacing, etc., may be modulated in a desired manner to achieve a desired plasma source material droplet formation as will be understood by those skilled in the art.

It will be understood that over time, this actuator 160 and its impact on, e.g., the capillary tube and thus droplet 172 formation may change. Therefore, according to aspects of an embodiment of the present invention, a sensor 180 may also be applied to the plasma source material formation and delivery system element, e.g., the capillary tube 152, e.g., in the vicinity of the actuator 160 to sense, e.g., the actual motion/vibration or the like applied to the, e.g., capillary tube by the actuator in response to an actuator signal 182 illustrated graphically in FIG. 4A.

A controller (not shown) may compare this actuator 160 input signal, e.g., of FIG. 3 with a sensor 180 output signal 184, to detect differences, e.g., in amplitude, phase, period, etc. indicating that the actual motion/vibration, etc. applied to the, e.g., capillary tube 152 measured by the sensor is not correlated to the applied signal 182, sufficiently to detract from proper droplet formation, size, velocity, spacing and the like. This is again dependent upon the structure actually used to modulate droplet formation parameters and the type of materials used, e.g., plasma source material, actuatable material, sensor material, structural materials, etc., as will be understood by those in the art.

Applicants have found through experimentation results of LPP with tin droplets indicate that the conversion efficiency may be impacted negatively by absorption of the produced EUV radiation in the plasma plume. This has led applicants to the conclusion that the tin droplet targets can be improved, according to aspects of an embodiment of the present invention, e.g., by being diluted by some means.

Additionally, according to testing by applicants a tin droplet jet may suffer from unstable operation, it is believed by applicants to be because the droplet generator temperature cannot be raised much above the melting point of tin (232° C.) in order not to damage associated control and metrology units, e.g., a piezo crystal used for droplet formation stimulation. A lower operating temperature (than the current temperature of 250° C.) would be beneficial for more stable operation.

According to aspects of an embodiment of the present invention, therefore, applicants propose to use, e.g., eutectic alloys containing tin as droplet targets. The droplet generator can then be operated at lower temperatures (below 250° C.). Otherwise, if the generator is operated at the same or nearly the same temperature as has been the case, i.e., at about 250° C., the alloy can, e.g., be made more viscous than the pure tin at this same temperature. This can, e.g., provide better operation of the droplet jet and lead to better droplet stability. In addition, the tin so diluted by other metal(s), should be beneficial for the plasma properties, especially, if, e.g., the atomic charge and mass number of the added material is lower than that of tin. applicants believe that it is better to add a lighter element(s) to the tin rather than a heavier element like Pb or Bi, since the LPP radiates preferentially at the transitions of the heaviest target element material. The heaviest element usually dominates the emission.

On the other hand, lead (Pb) for example does emit EUV radiation at 13.5 nm in LPP. Therefore, Pb and likely also Bi may be of use as admixtures, even though the plasma is then likely to be dominated by emission of these metals and there may be more out-of-band radiation.

Since the alloy mixture is eutectic, applicants believe there will be no segregation in the molt and all material melts together and is not separated in the molt. An alloy is eutectic when it has a single melting point for the mixture. This alloy melting point is often lower than the melting points of the various components of the alloy. The tin in the droplets is diluted by other target material(s). Applicants also believe that this will not change the plasma electron temperature by a great amount but should reduce EUV absorption of tin to some degree. Therefore, the conversion efficiency can be higher. This may be even more so, if a laser pre-pulse is used, since the lighter target element(s) may then be blown off faster in the initial plasma plume from the pre-pulse. These lighter atoms are also not expected to absorb the EUV radiation as much as the tin.

Indium is known to have EUV emission near 14 nm. Therefore, the indium-tin binary eutectic alloy should be quite useful. It has a low melting point of only 118° C. A potential disadvantage may be that now not only tin debris but also debris from the other target material(s) may have to be mitigated. However, for a HBr etching scheme it may be expected that for example indium (and some of the other elements proposed as alloy admixtures) can be etched pretty much in the same way as tin.

According to aspects of an embodiment of the present invention a tin droplet generator may be operated with other than pure tin, i.e., a tin containing liquid material, e.g., an eutectic alloy containing tin. The operating temperature of the droplet generator can be lower since the melting point of such alloys is generally lower than the melting point of tin. Appropriate tin-containing eutectic alloys that can be used are listed below, with the % admixtures and the associated melting point. For comparison with the above noted melting point of pure Sn, i.d., 232° C.

48 Sn/52 In (m. p. 118° C.),
91 Sn/9 Zn (m. p. 199° C.),
99.3 Sn/0.7 Cu (m. p. 227° C.),
93.6 Sn/3.5 Ag/0.9 Cu (m. p. 217° C.)
81 Sn/9 Zn/10 In (m. p. 178° C., which applicants believe to be eutectic
96.5 Sn/3.5 Ag (m. p. 221° C.),
93.5 Sn/3 Sb/2 Bi/1.5 Cu (m. p. 218° C.),
42 Sn/58 Bi (m. p. 138° C.,), can be dominated by emission from bismuth
63 Sn/37 Pb (m. p. 183° C., can be partly dominated by emission from lead
Sn/Zn/Al (m. p. 199° C.

Also useful may be Woods metal with a melting point of only 70° C., but it does not contain a lot of tin, predominantly it consists of Bi and Pb (Woods metal: 50 Bi/25 Pb/12.5 Cd/12.5 Sn).

It will be understood by those skilled in the art that an EUV light generation system and method is disclosed that may comprise a droplet generator producing plasma source material target, e.g., droplets of plasma source material or containing plasma source material within or combined with other material, e.g., in a droplet forming liquid. The droplets may be formed from a stream or on a droplet on demand basis, e.g., traveling toward the vicinity of a plasma source material target irradiation site. It will be understood that the plasma targets, e.g., droplets are desired to intersect the target droplet irradiation site but due to, e.g., changes in the operating system over time, e.g., drift in certain control system signals or parameters or actuators or the like, may drift from the desired plasma initiation (irradiation) site. The system and method, it will be understood, may have a drive laser aimed at the desired target irradiation site, which may be, e.g., at an optical focus of an optical EUV collector/redirector, e.g., at one focus of an elliptical mirror or aimed to intersect the incoming targets, e.g., droplets at a site in the vicinity of the desired irradiation site, e.g., while the control system redirects the droplets to the desired droplet irradiation site, e.g., at the focus. Either or both of the droplet delivery system and laser pointing and focusing system(s) may be controlled to move the intersection of the drive laser and droplets from a point in the vicinity of the desired plasma formation site (i.e., perfecting matching the plasma initiation site to the focus of the collector) to that site. For example, the target delivery system may drift over time and use and need to be corrected to properly deliver the droplets to the laser pointing and focusing system may direct the laser to intersect wayward droplets only in the vicinity of the ideal desired plasma initiation site, while the droplet delivery system is being controlled to correct the delivery of the droplets, in order to maintain some plasma initiations, thought the collection may be less than ideal, they may be satisfactory to deliver over dome time period an adequate dose of EUV light. Thus as used herein and in the appended claims, “in the vicinity” according to aspects of an embodiment of the present invention means that the droplet generation and delivery system need not aim or delivery every droplet to the ideal desired plasma initiation but only to the vicinity accounting for times when there is a error in the delivery to the precise ideal plasma initiation site and also while the system is correcting for that error, where the controls system, e.g., due to drift induced error is not on target with the target droplets and while the error correction in the system is stepping or walking the droplets the correct plasma initiation site. Also there will always be some control system jitter and the like or noise in the system that may cause the droplets not to be delivered to the precise desired target irradiation site of plasma initiation site, such that “in the vicinity” as used accounts for such positioning errors and corrections thereof by the system in operation.

The system may further comprise a drive laser focusing optical element having a first range of operating center wavelengths, e.g., at least one spectrum with a peak centered generally at a desired center wavelength in the EUV range. A droplet detection radiation source having a second range of operating center wavelengths may be provided, e.g., in the form of a relatively low power solid state laser light source or a HeNe laser. A laser steering mechanism, e.g., an optical steering element comprising a material that is highly reflective within at least some part of the first range of wavelengths and highly transmissive within at least some part of the second range of center wavelengths may be provided, e.g., a material that reflects the drive laser light into the EUV light source plasma production chamber and directly transmits target detection radiation into the chamber. A droplet detection aiming mechanism may also be provided, such as another optical element for directing the droplet detection radiation through the drive laser steering element and the a lens to focus the drive laser at a selected droplet irradiation site at or in the vicinity of the desired site, e.g., the focus. For example, the droplet detection aiming mechanism may change the angle of incidence of the droplet detection radiation on the laser beam steering element thus, e.g., directing it to a detection position intermediate the droplet generator and the irradiation site. Advantageously, e.g., the detection point may be selected to be a fixed separation in a selected direction from the selected irradiation site determined by the laser steering element as is selected by the change in the angle of the detection radiation on the steering optical element that steers the drive laser irradiation. The apparatus and method may further comprise a droplet detection mechanism that may comprise a droplet detection radiation detector, e.g., a photodetector sensitive to the detection radiation, e.g., HeNe laser light wavelength, e.g., positioned to detect droplet detection radiation reflected from a plasma source material droplet. The droplet detection radiation detector may be selected to be not sensitive to radiation within a second range of center wavelengths, e.g., the drive laser range of radiation wavelengths. The droplet detection radiation may be focused to a point at or near the selected droplet detection position such that the droplet detection radiation reflects from a respective plasma source material target at the selected droplet detection position.

The EUV plasma source material target delivery system may also comprise a plasma source material target formation mechanism which may comprise a plasma source target droplet formation mechanism comprising a flow passageway, e.g., a capillary tube and an output orifice, which may or may not form the output of a nozzle at the terminus of the flow passage. A stream control mechanism may be provided, e.g., comprising an energy imparting mechanism imparting stream formation control energy to the plasma source material droplet formation mechanism, e.g., in the form of moving, shaking, vibrating or the like the flow passage and/or nozzle or the like to at least in part control a characteristic of the formed droplet stream. This characteristic of the stream it will be understood at least in part determined the formation of droplets, either in an output jet stream or on a droplet on demand basis, or the like. An imparted energy sensing mechanism may be provided for sensing the energy actually imparted to the stream control mechanism, e.g., by detecting position, movement and/or vibration frequency or the like and providing an imparted energy error signal, e.g., indicating the difference between an expected position, movement and/or vibration frequency or the like and the actual position, movement and/or vibration frequency or the like. The target steering mechanism feedback signal may be used then to, e.g., modify the actual imparted actuation signal, e.g., to relocate the or re-impose the actual position, movement and/or vibration frequency or the like needed to, e.g., redirect plasma source material targets, e.g., droplets, by use, e.g., of a stream control mechanism responsive to the actuation signal imparted to the energy imparting mechanism and thereby cause the targets, e.g., to arrive at the desired irradiation site, be of the desired size, have the desired frequency and/or the desired spacing and the like.

It will be understood that such a system may be utilized to redirect the targets not due to operating errors, but, e.g., when it is desired to change a parameter, e.g., frequency of target delivery or the like, e.g., due to a change in duty cycle, e.g., for a system utilizing the EUV light, e.g., an integrated circuit lithography tool.

It will be understood by those skilled in the art that the aspects of embodiments of the present invention disclosed above are intended to be preferred embodiments only and not to limit the disclosure of the present invention(s) in any way and particularly not to a specific preferred embodiment alone. Many changes and modification can be made to the disclosed aspects of embodiments of the disclosed invention(s) that will be understood and appreciated by those skilled in the art. The appended claims are intended in scope and meaning to cover not only the disclosed aspects of embodiments of the present invention(s) but also such equivalents and other modifications and changes that would be apparent to those skilled in the art. In additions to changes and modifications to the disclosed and claimed aspects of embodiments of the present invention(s) noted above the following could be implemented.

We claim:

1. An EUV light generation system comprising:

a droplet generator producing plasma source material target droplets traveling toward the vicinity of a plasma source material target irradiation site;

a drive laser;

a drive laser focusing optical element having a first range of operating center wavelengths;

a droplet detection radiation source having a second range of operating center wavelengths;

a drive laser steering element comprising a material that is highly reflective within at least some part of the first range of wavelengths and highly transmissive within at least some part of the second range of center wavelengths;

a droplet detection radiation aiming mechanism directing the droplet detection radiation through the drive laser steering element and the lens to focus at a selected droplet detection position intermediate the droplet generator and the irradiation site.

2. The apparatus of claim 1 further comprising:

the droplet detection radiation source comprises a laser.

3. The apparatus of claim 1 further comprising:

the droplet detection radiation aiming mechanism comprising a mechanism selecting the angle of incidence of the droplet detection radiation on the drive laser steering element.

4. The apparatus of claim 2 further comprising:

the droplet detection radiation aiming mechanism comprising a mechanism selecting the angle of incidence of the droplet detection radiation on the drive laser steering element.

5. The apparatus of claim 3 further comprising:

the droplet detection radiation is focused to a point at or near the selected droplet detection position such that the droplet detection radiation reflects from a respective plasma source material target at the selected droplet detection position.

6. The apparatus of claim 4 further comprising:

the droplet detection radiation is focused to a point at or near the selected droplet detection position such that the droplet detection radiation reflects from a respective plasma source material target at the selected droplet detection position.

7. An EUV plasma source material target delivery system comprising:

a plasma source material target formation mechanism comprising;

a plasma source target droplet formation mechanism comprising a flow passageway and an output orifice;

a stream control mechanism comprising an energy imparting mechanism imparting stream formation control energy to the plasma source material droplet formation mechanism to at least in part control a characteristic of the formed droplet stream; and, an imparted energy sensing mechanism sensing the energy imparted to the stream control mechanism and providing an imparted energy error signal.

8. The apparatus of claim 7 further comprising:

the target steering mechanism feedback signal represents a difference between an actual energy imparted to the stream control mechanism and an actuation signal imparted to the energy imparting mechanism.

9. The apparatus of claim 7 further comprising:

the flow passageway comprising a capillary tube.

10. The apparatus of claim 8 further comprising:

the flow passageway comprising a capillary tube.

11. An LPP EUV light generating apparatus comprising:

a plasma source material target droplet delivery mechanism;

plasma source material comprising a eutectic alloy of a target material and another material.

* * * * *